(12) United States Patent
Embro

(10) Patent No.: US 6,605,289 B1
(45) Date of Patent: Aug. 12, 2003

(54) METHOD AND COMPOSITION FOR THE TREATMENT OF EPIDERMAL IRRITATIONS AND INFECTIONS

(75) Inventor: William J. Embro, Gainsville, FL (US)

(73) Assignee: Embro Research Company, LLC., Gainsville, FL (US)

( * ) Notice: Subject to any disclaimer, the term of this patent is extended or adjusted under 35 U.S.C. 154(b) by 0 days.

(21) Appl. No.: 09/701,498

(22) PCT Filed: Jun. 9, 1999

(86) PCT No.: PCT/US99/13048

§ 371 (c)(1),
(2), (4) Date: Dec. 21, 2000

(87) PCT Pub. No.: WO99/63816

PCT Pub. Date: Dec. 16, 1999

Related U.S. Application Data

(60) Provisional application No. 60/088,560, filed on Jun. 9, 1998.

(51) Int. Cl.⁷ .......................... A61K 7/00; A01N 25/00
(52) U.S. Cl. ....................................... 424/401; 424/405
(58) Field of Search ................................. 424/401, 405

(56) References Cited

U.S. PATENT DOCUMENTS

| | | | | |
|---|---|---|---|---|
| 4,415,590 A | * | 11/1983 | Gerzon | 424/319 |
| 4,469,674 A | * | 9/1984 | Shah et al. | 424/52 |
| 5,094,845 A | * | 3/1992 | Vlock | 424/52 |
| 5,098,716 A | * | 3/1992 | Embro | 424/650 |
| 5,416,075 A | | 5/1995 | Carson et al. | 514/23 |
| 5,672,351 A | | 9/1997 | Chikindas et al. | 424/401 |
| 5,965,610 A | * | 10/1999 | Modak et al. | 514/494 |

OTHER PUBLICATIONS

Gennaro, ed. Remington: the Science and Practice of Pharmacy Chapters 52 and 80, pp. 873 and 1396.*

* cited by examiner

*Primary Examiner*—Thurman K. Page
*Assistant Examiner*—Todd D Ware
(74) *Attorney, Agent, or Firm*—Fulbright & Jaworski L.L.P.

(57) ABSTRACT

A stannous fluoride composition is disclosed. The composition comprises stannous fluoride and at least one zinc containing compound. The zinc containing compounds stabilize and prevent hydrolysis of the stannous ions resulting in a stannous fluoride composition for use in the treatment of epidermal irritations and infections.

4 Claims, No Drawings

METHOD AND COMPOSITION FOR THE TREATMENT OF EPIDERMAL IRRITATIONS AND INFECTIONS

This application is A 371 OF PCT/US99/13048 Jun. 9, 1999 which claims benefit of Ser. No. 60/088,560 Jun. 9, 1998.

FIELD OF THE INVENTION

The present invention relates to an improved stannous fluoride composition for the treatment of epidermal irritations and infections.

BACKGROUND OF THE INVENTION

Stannous fluoride has been used in dentistry since the 1950's to prevent dental cavities. Norman Tinanoff outlines 40 years of human and animal studies with some studies having greater efficacy than others in "Review of the Antimicrobial Action of Stannous Fluoride" (The Journal of Clinical Dentistry Vol. II 1990). U.S. Pat. No. 4,097,590 "Methods and Compositions for Treatment of Bacteria and Fungus infections of the skin" discloses treatment for vulgaris and athletes foot with a soluble fluoride salt. The present inventor previously determined that stannous fluoride can be used for treating diseases having viral etiology. (U.S. Pat. No. 5,098,716 to Embro).

Both the shelf life and antimicrobial effect of a stannous fluoride product depend on stability of the active stannous ion (Sn+2). Products formulated for home use achieve stability of the stannous ion by adding glycerin or other water-insoluble materials to reduce hydrolysis and oxidation. Aqueous formulations employed chelating agents which bind stannous fluoride and create a stannous reservoir that acts both as a supply of stannous ions and an antioxidant. Majeti et. al. (U.S. Pat. No. 5,004,597), developed a dentifrice stabilization system for stannous fluoride by utilizing stannous chloride as an antioxidant with stannous reservoir and sodium gluconate as a chelating agent to protect stannous fluoride from hydrolysis. Other chemicals used in stannous fluoride stabilization include polyvinyl alcohol (PVA), tripolyphosphates, copolymers of vinylmethylether and maleic anhydride. However, the use of these and other complexing agents for stannous fluoride stabilization can limit the bioavailability of stannous ions for a therapeutic effect.

In view of the foregoing, there is a need to provide improved stannous fluoride compositions.

SUMMARY OF THE INVENTION

The present invention relates to an improved stannous fluoride composition comprising stannous fluoride and at least one zinc containing compound. The inventor has shown that the improved composition is more stable and less toxic than a stannous fluoride composition that does not contain a zinc compound. The inventor has also shown that the improved composition of the invention allows one to decrease the dose of stannous fluoride required to achieve a therapeutic effect.

The inventor has demonstrated that the improved composition of the invention is effective in treating epidermal irritations and infections and their symptoms. Accordingly, the present invention also provides a method of treating an epidermal irritation or infection comprising administering an effective amount of a composition comprising stannous fluoride and at least one zinc containing compound to an animal in need thereof.

Other features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

DETAILED DESCRIPTION OF THE INVENTION COMPOSITIONS OF THE INVENTION

The present invention relates to an improved stannous fluoride composition comprising stannous fluoride and at least one zinc containing compound. This composition may be referred to herein as "the composition of the invention".

The composition of the invention is markedly improved over a composition containing stannous fluoride without any zinc compounds in several respects. Firstly, stannous fluoride undergoes hydrolysis and oxidation in aqueous environments which results in the loss of stannous bioavailability due to the precipitation of stannous hydroxide. The zinc containing compounds stabilize the stannous fluoride by preventing the oxidation and hydrolysis of the stannous ion. Zinc ions have a greater affinity than stannous ions for hydroxides and other anions in aqueous solutions. As a result the zinc in the composition of the invention will complex the hydroxides and inhibit hydrolysis and precipitation of the stannous ions. In particular, the inventor has demonstrated that a stannous fluoride solution containing zinc gluconate remained stable, without precipitation, for at least 3 months. In contrast, a stannous fluoride solution without zinc gluconate extensively precipitated. Secondly, the zinc compounds buffer the hydrogen ion which promotes an elevated pH. This makes the composition more suitable for topical use as more acidic formulations can irritate or cause a burning sensation of the skin. Thirdly, the present inventor has unexpectedly found that the zinc compounds act synergistically with and potentiate the activity of the stannous fluoride. In particular, the present inventor has demonstrated that in the composition of the invention the stannous fluoride works better than when twice the dose is used in a composition that does not contain the zinc compounds. Consequently, the dose of the stannous fluoride can be significantly lowered in the composition of the invention resulting in a less toxic composition.

As mentioned above, inclusion of zinc compounds in the composition of the present invention stabilizes and enhances the efficacy of the stannous fluoride. Using zinc containing compounds in the composition also has additional advantages in that zinc is widely recognized as having medicinal and healing properties. In particular, 1) zinc is essential for life; 2) zinc is necessary for over 100 enzymes (i.e., alcohol dehydrogenase carboxypeptidase); 3) zinc maintains body levels of Vitamin A; 4) zinc is important in sex organ function and reproduction; 5) zinc is important for DNA/RNA synthesis; 6) zinc can improve cell-mediated immunity; and 7) zinc is incorporated in hundreds of dermatological formulas to help maintain healthy skin cells. Using stannous compounds with the stannous fluoride will not provide the added benefits that zinc does as stannous is not essential for life and is not necessary for enzyme function.

The zinc containing compound can be any compound containing zinc including zinc carboxylates and zinc salts. The zinc carboxylate is preferably selected from one or more of zinc gluconate, zinc tartrate, zinc malate, zinc propionate, zinc citrate and zinc acetate. More preferably, the zinc carboxylate is zinc gluconate. The zinc salt is preferably selected from zinc chloride, zinc sulfate, zinc phosphate, zinc pyrophosphate, zinc oxide or zinc thiocynate. Preferably, the zinc salt is zinc chloride.

The composition of the invention preferably comprises stannous fluoride in a concentration ranging from about 0.01 wt % to about 10.0 wt % and one or more zinc containing compound in an amount from about 0.05 wt % to about 20.0 wt %.

In a preferred embodiment, the composition comprises stannous fluoride and zinc gluconate. The inventor has shown that a composition comprising stannous fluoride and zinc gluconate provides significantly greater efficacy in the treatment of a viral, bacterial and fungal infections as compared to a stannous fluoride composition alone. In particular, the inventor has demonstrated that with the improved composition one can use one half the amount of stannous fluoride as is used in a composition containing stannous fluoride alone with improved results.

Preferably, the stannous fluoride is provided in a concentration ranging from about 0.1 wt. % to about 8.0 wt. % and zinc gluconate is provided in concentration ranging from about 0.5 wt. % to about 10.0 wt. %. Most preferably, the composition comprises 0.20 % stannous fluoride and 1.5% zinc gluconate, in a non-aqueous medium such as glycerin.

The composition may additionally contain zinc chloride in a concentration ranging from about 0.5 wt. % to about 5.0 wt. %. The addition of zinc chloride may be useful in compositions with a high aqueous content (i.e. >80% water).

The composition of the invention can include more than one zinc containing compound. For example, the zinc compound may be zinc gluconate, zinc chloride and/or zinc acetate.

The composition may additionally include one of the essential or non-essential α, L or D amino acids selected from the group consisting of lysine, arginine, histidine, phenylalanine, threonine, leucine, isoluceine, cysteine, methionine, valine, alanine, glycine, proline, glutamine, serine, tryptophan, tyrosine and asparagine.

The composition can be formulated using techniques known in the art for example as described in Remington's Pharmaceutical Sciences, Eighteenth Edition, Mack Publishing Company. The composition is preferably a gel, ointment, cream, lotion, spray or the like, suitable for topical administration. Advantageously, the composition of the present invention maintains its bioavailability at a pH suitable for topical administration. The composition may also include pharmaceutically acceptable diluents or carriers including water, carbopol, glycerin and hydroxymethyl cellulose.

The composition of the invention may additionally include excipients known in the art including fillers such as saccharides, for example, lactose or sucrose, mannitol or sorbitol cellulose preparations and/or calcium phosphates, for example, tricalcium phosphate or calcium hydrogen phosphate, as well as binders such as starch paste, using for example, maize starch, wheat starch, rice starch, potato starch, gelatin, tragacanth, methyl cellulose, hydroxypropylmethylcellulose, sodium carboxymethylcellulose, and/or polyvinyl pyrrolidone. In some cases, it may be desirable to add disintegrating agents such as the above mentioned starches and also carboxymethyl-starch, cross-linked polyvinyl pyrrolidone, agar, or alginic acid or a salt thereof, such as sodium alginate. Auxiliaries are, above all, flow-regulating agents and lubricants, for example, silica, talc, steric acid or salts thereof, such as magnesium stearate or calcium stearate, and/or polyethylene glycol.

The compositions of the invention may contain, as additives, preservatives such as p-hydrobenzoates (nipa esters, methylparaben), sorbic acid, chlorhexidine digluconate, benzalkonium chloride and hexadecyltrimethyl ammonium bromide.

In order to accelerate the absorption of the composition through the skin, permeation accelerators such as dimethylsulfoxide or ttauroglycolic acid may be added to the composition.

Hydrogel forming agents which may be used include gelatine and cellulose derivatives such as methyulcellulose, hydroxypropylcellulose and hydroxyethylcellose, as well as synthetic polymers such as polyvinyl alcohol. The nature and quantity of the hydrogel forming agents used or the mixtures thereof will depend on the particular viscosity required.

The additives which may be present also include moisture-retaining substances such as glycerol, sorbitol, 1,2-propyleneglycol, butyleneglycol and polyols.

USES OF THE COMPOSITIONS

The inventor has demonstrated that the improved composition of the invention is effective in treating epidermal irritations and infections and their symptoms. Accordingly, the present invention also provides a method of treating an epidermal irritation or infection comprising administering an effective amount of a composition comprising stannous fluoride and at least one zinc containing compound to an animal in need thereof. The zinc containing compound is preferably zinc gluconate and may optionally include zinc chloride.

The term "effective amount" means providing an amount at dosages and for periods of time that is effective to achieve the desired result. The frequency of application of the composition of the invention may range anywhere from one to six times a day, or as needed for the healing process. The course of the therapy typically ranges from one to six times a day, for several days, and may be continued as long as required for complete relief.

The term "animal" as used herein includes all members of the animal kingdom. Preferably, the animal is a mammal such as a human, horse, dog or cat.

The term "epidermal irritation" means any condition that adversely affects or irritates the skin or coat of an animal including, but not limited to, insect bites, fleas, burns, psoriasis, dermatitis, acne and epidermal infections such as subcutaneous mycoses (sporotrichosis, phycomycosis, phacohypomycosis); Cutaneous Habronemiasis; Cutaneous Onchocerciasis (Onchocerca cervicalis); Seborrhea; Dermatophilosis (Dermatophilus congolensis); Dermatophytosis (Trichophyton equinum, Trichophyton mentagrophytes, Trichophyton verrucosum); Warble fly larvae (Hypoderma spp); or Bot fly larvae (Gasterophilus nasalis/Gasterophilus hemorradalis).

The term "infection" means any infection including, but not limited to, viral, bacterial, fungal and parasitic infections, that affects animals.

The viral infections that may be treated using the composition of the invention include herpes viruses such as Herpes Simplex I which causes cold sores and Herpes Zoster which causes shingles; Epstein-Barr virus; Papilloma virus which causes warts; cytomegalovirus; hepatitis virus; varicella-zoster virus which causes chicken pox; cold and flu viruses; human and feline leukemia viruses; human immunodeficiency viruses (HIVs) and viruses that cause ringworm.

The bacterial infections that may be treated using the composition of the invention include Streptococcus, Staphlococcus and Dermatophilus skin infections as well as mycoplasmas related to chronic sinus infections.

The fungal infections that may be treated using the composition of the invention include yeast infections of the oral cavity and vagina; fungal infections of the fingernails and feed (athletes foot); and fungal infections of the horse and cow epidermis including infections caused by the genera Microsporum and Trichophyton.

The composition of the invention is particularly well suited for the treatment of epidermal infections such as infections of the skin as well as ocular or eye infections. The inventor has shown that the composition is effective in treating many infections in human patients as well as in other mammals including horses, cats and dogs.

The present invention also provides a use of a composition comprising stannous fluoride and at least one zinc containing compound to treat an epidermal irritation or infection. The invention further provides a use of a composition comprising stannous fluoride and at least one zinc containing compound to prepare a medicament to treat an epidermal irritation or infection.

The following non-limiting examples are illustrative of the present invention:

EXAMPLES

Example 1

A composition of the present invention comprising stannous fluoride (0.2%) and zinc gluconate (1.5%) was compared to a composition containing stannous fluoride (0.4%) on the ability to treat cold sores caused by herpes virus. A placebo containing glycerin only was also prepared. Each composition was tested on 10 patients. The results, shown in Table 1, demonstrate that the average healing time for the group receiving stannous fluoride with zinc gluconate was 4.2 days as compared to 5.9 days for the group receiving stannous fluoride alone. This is a significant reduction in healing time. In addition, the composition containing zinc gluconate contained one half the amount of stannous fluoride as compared to the stannous fluoride alone composition. Consequently, the composition of the present invention provides a much more efficacious composition as evidenced by the reduced healing time and reduced amount of stannous fluoride required.

Example 2

Five horses infected by the bacterium, Dermatophilus congolensis (commonly known as rain scald) were cured when several applications of a 0.2% stannous fluoride/1.5% zinc gluconate gel was applied over a period of two weeks.

Example 3

Five horses infected by fungi of the genera Microsporum and Trichophyton received immediate relief and were cured of the infection in a one week period when treated with a 0.2% stannous fluoride/1.5% zinc gluconate gel.

Example 4

Five colts suffering from warts (papilloma virus) on the muzzle, were successfully cured of the disease by applying a 0.2% stannous fluoride/1.5% zinc gluconate gel to the affected area several times a day for two weeks. There was no scarring.

Example 5

Several equines were successfully treated for pastern dermatitis (grease heel, scratches, mud fever) the cause of a staphlococcus/streptococcus/ Dermatophilus infection with topical and bandaged applications of a 0.2% stannous fluoride/1.5% zinc gluconate gel.

Example 6

Several cats were treated to control ringworm and oral facial sores of viral etiology with a 0.2% stannous fluoride/1.5% zinc gluconate gel.

Example 7

Several dogs with bacterial skin infections the result of intense scratching due to insect bites were successfully treated with several applications of a 0.2% stannous fluoride/1.5% zinc gluconate gel.

Example 8

A patient, burned with candle wax flame resulting in a six inch diameter burn area, used two applications of a 0.2% stannous fluoride/1.5% zinc gluconate gel daily. As a result, the patient did not require the use of pain medication and antibiotics for infection. The composition not only relieved severe pain but also prevented blistering and infection. The area was totally healed in less than three weeks with minimal scarring.

Example 9

A patient burned on an electric heating coil of a stove did not blister after an immediate application of a 0.2% stannous fluoride/1.5% zinc gluconate gel. The patient did not scab and the area did not get infected.

Example 10

Other skin ailments successfully treated with several applications of a 0.2% stannous fluoride/1.5% zinc gluconate gel, include acne, infected bug bites, warts, ringworm, and psoriasis. It appears that the antimicrobial effect of stannous fluoride and the immune stimulatory properties of zinc gluconate synergistically enhance healing due to microbial infections.

Example 11

Treatment of Herpes

A composition of the present invention comprising 0.2% stannous fluoride; 0.2% zinc chloride and 1.5% zinc gluconate and the remainder glycerin was compared to a 0.4% stannous fluoride in glycerin composition in the treatment of herpes simplex virus I (cold sores). The study consisted of two groups of 10 healthy adults with cold sores. One group was treated with the composition containing the zinc compounds and the second group with the stannous fluoride alone composition. The adults treated with the composition containing the zinc compounds had a mean healing time of 3.1 days while the group treated with the stannous fluoride alone had a mean healing time of 3.9 days. As a result, the group treated with the composition of the invention that contained one half the amount of stannous fluoride as the other composition, healed at a faster rate. This study illustrates that the composition of the invention treats herpes infections with much greater efficacy than a composition containing stannous fluoride alone.

Example 12
Treatment of Shingles

The composition of Example 11 was used to treat several patients having a shingles outbreak. The patients reported a relief of pain and fast healing when treated with the composition of the invention. In addition, when compared with a composition containing stannous fluoride alone, the patients reported less burning with the composition of the invention.

Example 13
Treatment of Bacterial Infections

One patient was treated with the composition of Example 11 for impetigo which is a streptococcus infection of the skin. The treatment was successful. Another patient used a gel formulation of the present invention to control a resistant staphococcus skin infection.

Example 14
Treatment of Cold and Flu

The composition of Example 11 was used to successfully treat sore throats associated with colds and flu.

Example 15
Treatment of Mycoplasma Infection

The composition of Example 11 was used to successfully treat mycoplasmas related to a chronic sinus infection.

Example 16
Treatment of Fungal Infections

Fungal infections associated with human fingernails and feet (athlete's foot), and horse and cow epidermis as well as fungal infections of the oral cavity and vagina were successfully treated with the composition of Example 11.

Example 17
Treatment of Cat Oral Ulcers

Cat oral ulcers of viral and rickettsial origin resulted in fast healing when the composition of Example 11 was applied several times.

Example 18
Treatment of Horses

The composition of Example 11 has been used to treat many show horses for ringworm, papilloma virus, warts on the nose and parasitic irritations including mites and fly bites. All treatments were successful.

Example 19
Treatment of Bovines

The composition of Example 11 has been used to treat bovine skin conditions.

Example 20
Preparation of the Compositions of the Invention

To prepare the compositions of the invention all pharmaceutical mediums are heated to 150° F. and percolated with nitrogen gas to displace oxygen and eliminate water so that the stannous ion is free from oxidation and hydrolysis during the mixing process of stannous fluoride with zinc compounds. Suitable pharmaceutically accepted vehicles may be used separately or in combination include glycerin, water, ethanol, polyethylene glycol, polypropylene glycol, and the like. The following provides specific formulations that are within the scope of the present invention.

| Component | Percent by weight |
|---|---|
| Stannous fluoride | 0.20 |
| Zinc gluconate | 1.50 |
| Glycerin | 98.30 |
| Stannous fluoride | 0.20 |
| Zinc gluconate | 2.50 |
| Zinc chloride | 0.50 |
| Glycerin | 96.80 |
| Stannous fluoride | 0.20 |
| Zinc acetate | 2.50 |
| Zinc chloride | 0.50 |
| Glycerin | 96.80 |
| Stannous fluoride | 0.20 |
| Zinc gluconate | 2.80 |
| Zinc chloride | 0.50 |
| L-Lysine | 15.50 |
| Glycerin | 75.00 |
| Carbopol | 6.00 |
| Stannous fluoride | 0.25 |
| Zinc gluconate | 1.50 |
| Zinc chloride | 0.50 |
| Glycerin | 92.50 |
| Carbopol | 3.00 |
| Stannous fluoride | 0.20 |
| Zinc propionate | 2.50 |
| Zinc chloride | 0.50 |
| Glycerin | 96.80 |
| Stannous fluoride | 0.20 |
| Zinc propionate | 2.50 |
| Zinc chloride | 0.50 |
| Glycerin | 97.30 |
| Stannous fluoride | 0.25 |
| Zinc gluconate | 2.25 |
| Zinc chloride | 0.50 |
| Hydroxymethyl cellulose | 30.25 |
| Glycerin | 65.50 |
| Carbopol | 3.25 |

While the present invention has been described with reference to what are presently considered to be the preferred examples, it is to be understood that the invention is not limited to the disclosed examples. To the contrary, the invention is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

TABLE 1

| | Healing Time (days) | | |
|---|---|---|---|
| | SnF2 + ZnGlu | SnF2 | Placebo |
| | 5 | 6 | 7 |
| | 8 | 9 | 11 |
| | 4 | 5 | 6 |
| | 3 | 4 | 4 |
| | 4 | 8 | 7 |
| | 5 | 6 | 8 |
| | 3 | 4 | 9 |
| | 2 | 4 | 6 |
| | 3 | 6 | 10 |
| | 5 | 7 | 4 |
| Mean = | 4.2 | 5.9 | 7.2 |

I claim:
1. A method of treating a fungal infection consisting of topically administering an effective amount of a composition consisting of water, stannous fluoride and zinc gluconate in an amount sufficient to prevent oxidation and hydrolysis of the stannous ion for at least three months to an animal afflicted with a fungal infection that can be treated or alleviated with stannous ion.

2. The method according to claim 1 wherein the fungal infection is caused by Microsporum or Trichophyton.

3. The method according to claim 1 wherein the animal is a human.

4. The method according to claim 1 wherein the animal is a horse, cat or dog.

* * * * *